United States Patent

Garzon et al.

[11] Patent Number: 5,543,025
[45] Date of Patent: Aug. 6, 1996

[54] SOLID STATE OXYGEN SENSOR

[75] Inventors: Fernando H. Garzon, Sante Fe; Brandon W. Chung, Los Alamos; Ian D. Raistrick, Los Alamos; Eric L. Brosha, Los Alamos, all of N.M.

[73] Assignee: The Regents of the University of California, Office of Technology Transfer, Alameda, Calif.

[21] Appl. No.: 381,609

[22] Filed: Jan. 30, 1995

[51] Int. Cl.⁶ .................................................. G01N 27/26
[52] U.S. Cl. ........................ 204/425; 204/421; 204/424; 204/425; 204/431; 204/415
[58] Field of Search .................................. 204/421, 424, 204/425, 426, 427, 429, 431, 415

[56] References Cited

U.S. PATENT DOCUMENTS

| | | | |
|---|---|---|---|
| 4,710,848 | 12/1987 | Schlechtriemen et al. | 361/280 |
| 4,792,752 | 12/1988 | Schlechtriemen et al. | 324/71.1 |
| 4,931,214 | 6/1990 | Worrell et al. | 252/520 |
| 5,023,153 | 6/1991 | Weppner | 429/40 |
| 5,298,235 | 3/1994 | Worrell et al. | 429/33 |
| 5,332,483 | 7/1994 | Gordon | 429/30 |
| 5,378,345 | 1/1995 | Taylor et al. | 204/424 |
| 5,393,397 | 2/1995 | Fukaya et al. | 204/424 |
| 5,397,443 | 3/1995 | Michaels | 204/59 R |

OTHER PUBLICATIONS

W. Weppner, "Tetragonal Zirconia Polycrystals–A High Performance Solid Oxygen Ion Conductor," Solid State Ionics 52, 15–21 (1992).

*Primary Examiner*—Bruce F. Bell
*Attorney, Agent, or Firm*—Ray G. Wilson

[57] ABSTRACT

Solid state oxygen sensors are provided with a yttria-doped zirconia as an electrolyte and use the electrochemical oxygen pumping of the zirconia electrolyte. A linear relationship between oxygen concentration and the voltage arising at a current plateau occurs when oxygen accessing the electrolyte is limited by a diffusion barrier. A diffusion barrier is formed herein with a mixed electronic and oxygen ion-conducting membrane of lanthanum-containing perovskite or zirconia-containing fluorite. A heater may be used to maintain an adequate oxygen diffusion coefficient in the mixed conducting layer.

14 Claims, 3 Drawing Sheets

SOLID STATE OXYGEN SENSOR

This invention was made with government support under Contract No. W-7405-ENG-36 awarded by the U.S. Department of Energy. The government has certain rights in the invention.

BACKGROUND OF THE INVENTION

This invention relates to oxygen sensors and, more particularly, to solid-state oxygen sensors.

An electrochemical zirconia solid electrolyte oxygen sensor has been used for monitoring oxygen concentration in various applications, such as automobiles, to monitor exhaust gas composition and control air-to-fuel ratio for reducing harmful emission components and improving fuel economy. Solid-state electrochemical zirconia oxygen sensors are divided into two groups: (1) potentiometric or logarithmic air/fuel sensors; and (2) amperometric or linear air/fuel sensors. Potentiometric sensors are ideally suited to monitor the air-to-fuel ratio close to the complete combustion stoichiometry—a value of about 14.8 to 1 by volume. However, the potentiometric sensor is not very sensitive to changes in oxygen partial pressure away from this point because of the logarithmic dependence of the EMF on the oxygen partial pressure.

It is advantageous to operate gasoline power piston engines with excess oxygen to improve fuel economy and reduce hydrocarbon emissions. To maintain stable combustion away from stoichiometry and enable engines to operate in the excess oxygen (lean burn) region, several limiting-current amperometric sensors have been reported. These sensors typically show reproducible limiting current plateaus with an applied voltage caused by gas diffusion overpotential at the cathode. The sensor current plateau is generally linearly proportional to the concentration of oxygen in the external environment and the oxygen concentration. These characteristics are obtained by limiting the diffusion of oxygen through a gas diffusion barrier.

Two types of gas diffusion barriers are currently being evaluated: (1) a cavity with a small diffusion hole; and (2) a porous ceramic layer on the cathode to limit the oxygen transfer rate from the ambient gas. The aperture-type is relatively difficult to manufacture and requires that the aperture remain unplugged. The porous-type is easy to manufacture, but control of the porosity is difficult and the ceramic may provide a changing pore morphology over time.

W. Weppner, "Tetragonal Zirconia Polycrystals—A High Performance Solid Oxygen Ion Conductor," Solid State Ionics 52, 15–21 (1992), suggests that a solid mixed oxygen ion and electronic conductor might be tried to replace an aperture, where the material has a suitable diffusion constant for oxygen. However, there is no teaching about acceptable materials and design parameters for use with solid state electrolytes, e.g., tetragonal zirconia polycrystals (TZP) or cubic stabilized zirconia (CSZ), which are both forms of yttria-doped zirconia.

In accordance with the present invention, suitable solid mixed oxygen ion and electronic conductors are provided and operating conditions are established.

Accordingly, it is an object of the present invention to provide materials as solid mixed oxygen ion and electronic conductors for use in a solid-state oxygen sensor.

Another object of the present invention is to determine suitable operating parameters for oxygen sensors with solid oxygen ion and electronic conductors to provide suitable sensitivity.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise a solid-state oxygen sensor. The oxygen sensor is formed from a dense diffusion barrier of a mixed solid oxygen ion and electronic conductor that is disposed on a solid oxide electrolyte substrate. A suitable mixed conductor is a perovskite mixed conductor, e.g., a lanthanum-containing perovskite mixed conductor or a zirconia-containing fluorite mixed conductor, e.g., terbia-doped zirconia. The solid oxide electrolyte is preferably a stabilized zirconia, e.g., yttria-doped zirconia.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Solid state oxygen sensors that use zirconia for an electrolyte are based on the electrochemical oxygen pumping of a zirconia electrolyte. These sensors show reproducible limiting current plateaus with an applied voltage caused by the gas diffusion overpotential at the cathode. The sensor plateau is linearly proportional to the concentration of oxygen in the external environment. This phenomenon occurs because the diffusion of the oxygen through a gas diffusion barrier, e.g., a pinhole barrier or a porous layer, as used in prior art devices, is the rate-determining step. In accordance with the present invention, the diffusion barrier is formed with a mixed electronic and oxygen ion-conducting solid membrane. The diffusion of oxygen through the mixed conducting solid material is much slower than through a gas and improved sensor performance is obtained without the problems of the prior art. Further, the mixed conductor is also a very good electronic conductor and acts as a cathode with the charge transfer reaction occurring across the entire mixed conductor and electrolyte interfacial area. While this basic concept has been suggested, we have found particular mixed conductors and operating parameters that provide a linear relationship between the voltage at a limiting current and oxygen concentration in an applied gas.

Figure 1:
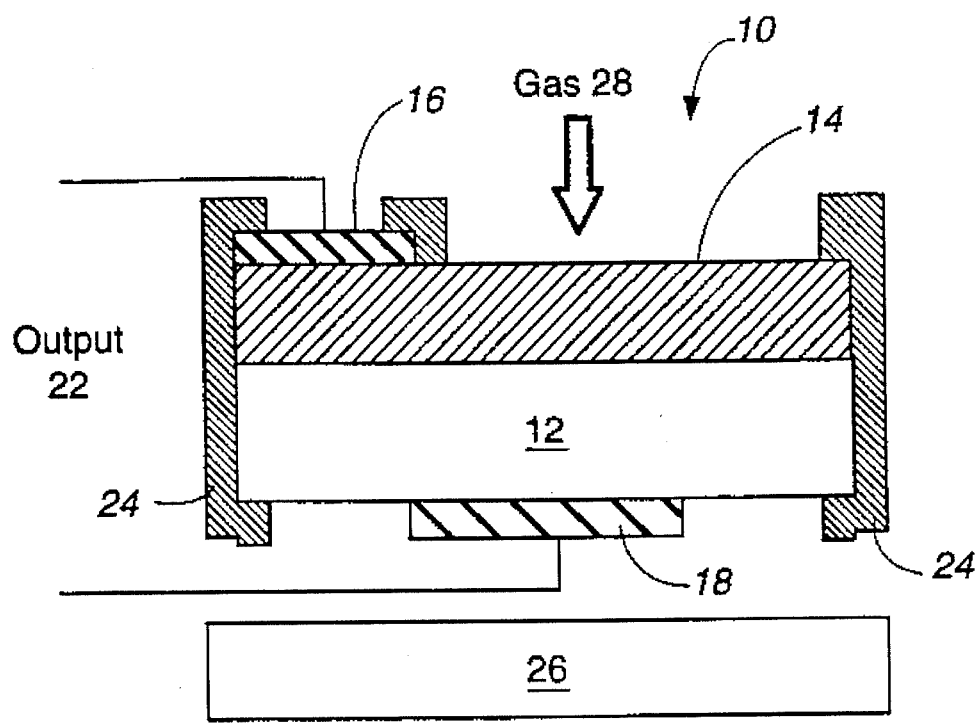
FIG. 1 is a cross-sectional view of one embodiment of an oxygen sensor according to the present invention.
Figure 2:
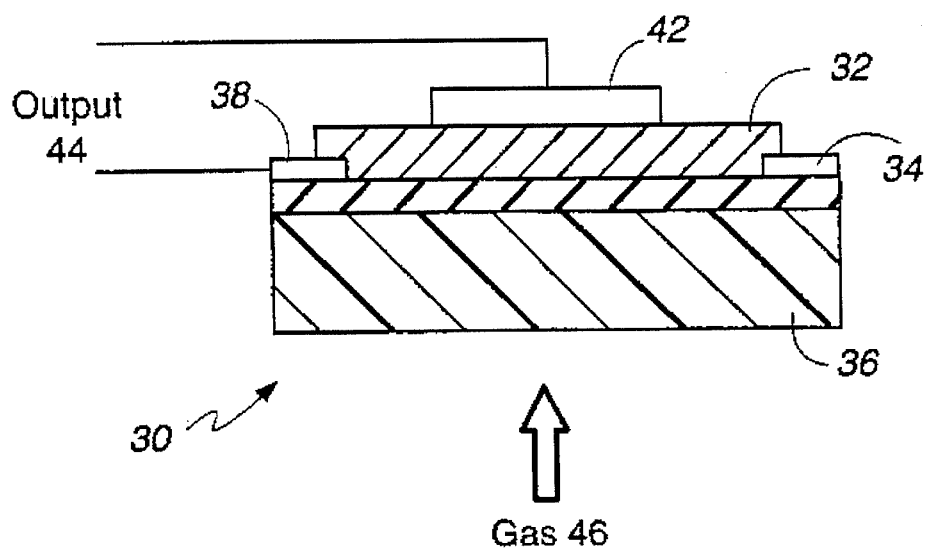
FIG. 2 is a cross-sectional view of a second embodiment of an oxygen sensor according to the present invention.

FIGS. 1 and 2 show cross-sections of exemplary solid-state oxygen sensors according to our invention. FIG. 1 depicts oxygen sensor 10 having a solid electrolyte 12 substrate with an overlying membrane of a mixed conductor 14. Electrode pads 16, 18, e.g., Pt electrodes, are in contact with mixed conductor 14 and electrolyte 12, respectively. The application of a gas 28 that contains oxygen will produce a limiting current output 22 as a dc potential is applied across the sensor, where the limiting current is linearly related to the concentration of oxygen in gas 28. In some instances, heater 26 may be provided to maintain an adequate diffusion coefficient in the mixed conducting layer 14.

Electrolyte 12 was formed from yttria-doped zirconia substrates obtained from A. C. Rochester and Enprotech respectively. Typical thicknesses of the yttria-doped zirconia substrates were 0.07 cm and 0.05 cm. The mixed conductors were formed from hot-pressed targets of $La_{0.84}Sr_{0.16}MnO_3$ (LSMO) and $La_{0.8}Sr_{0.2}CoO_3$ (LSCO) (Seattle Specialty Ceramics). The mixed conductors were deposited by a 90° off-axis radio-frequency (rf) magnetron sputtering technique. The depositions were done at an rf power of 100 W at a temperature of 700° C. Pt electrode pads 16, 18 were applied by sputtering. Glass seals 24 were applied to minimize electrochemical oxygen leakage.

FIG. 2 depicts a cross-sectional view of an alternate thin film embodiment of an oxygen sensor 30. Sensor 30 includes mixed conductor 34 deposited on a porous substrate 36, which may be $Al_2O_3$, and a film of an electrolyte 32 deposited on the mixed conductor layer. Electrode pads 38, 42 are suitably deposited on mixed conductor 34 and electrolyte 32, respectively. Gas 46 containing an oxygen content is sampled through porous substrate 36 and a current plateau output 44 is provided. It will be understood that the position of electrolyte 32 and mixed conductor 34 may be reversed, whereby gas 46 is incident directly on mixed conductor 34.

Figure 3:
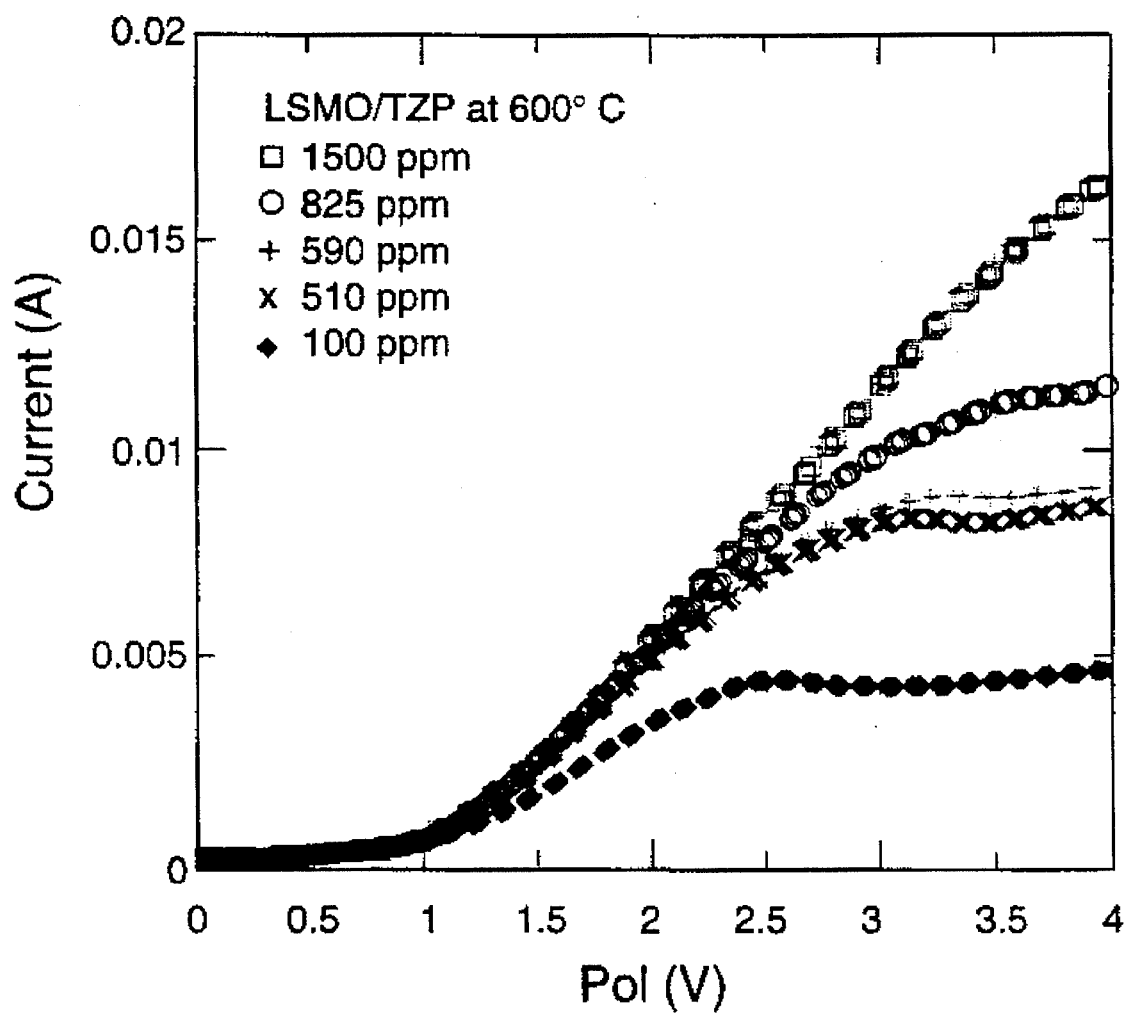
FIG. 3 graphically illustrates sensor i-V characteristics with limiting current plateaus at various oxygen concentrations.

FIG. 3 graphically illustrates the sensor i-V characteristics with limiting current plateaus at various oxygen concentrations. FIG. 3 is specifically for a LSMO mixed conductor on a yttria-doped zirconia substrate operating at 600° C. The gas mixture was oxygen and argon with controlled oxygen pressures, ranging from 0.01 to 20%. The oxygen partial pressure was fixed and measured using an Ametek oxygen analyzer. The sensors were connected to a Solartron 1286 Electrochemical Interface potentiostat and polarization potentials were incremented from 0–4 volts and the corresponding electrochemical current was recorded for each device. A set of data was taken at different furnace temperatures.

The i-V characteristic curves of a typical sensor according to our invention, exemplified by FIG. 3, has four regimes that represent different electroactive processes. In the beginning, the current increases exponentially with the applied voltage, perhaps due to a charge transfer reaction at the mixed conductor and solid electrolyte interface. The second regime shows an ohmic behavior in which the output current increases with increasing applied voltage due to the combined ionic transport in the mixed conductor and the solid electrolyte. Because the mixed conductors have electronic and oxygen ion conductivities that are several orders of magnitude higher than those of the solid electrolyte, the slopes are predominantly caused by the ohmic behavior of the solid electrolyte.

The third regime features the limiting current plateau, which is determined by the gas diffusion through the mixed conductor diffusion barrier. This current can be described using the following relationship:

$$i_l = \frac{4FD_{O_2}SC_{O_2}(0)}{L} \quad (1)$$

Where $i_1$, F, $D_{O2}$, S, $C_{O2}(0)$, and L are the limiting current, the Faraday constant, the oxygen diffusion coefficient through the mixed conductor at a given temperature, the surface area of the mixed conductor (diffusion barrier), the oxygen concentration in the ambient gas, and the thickness of the mixed conductor, respectively.

In the limiting-current plateau region, the rate determining step is based on the diffusion of oxygen atoms through the lattice of the mixed conductors. Since the electronic conductivity of mixed conductors is so high, the gradient of electrical potential is very small. Therefore, oxygen transport through these materials occurs only due to an oxygen chemical potential gradient. FIG. 3 shows that the limiting current plateaus have a slight slope with increasing applied voltage, believed to be caused by a mixture of ohmic current proportional to the applied voltage and by a current based on the diffusion restriction of atomic oxygen through the mixed conductors. The ohmic current is caused by electrochemical leakage around the solid electrolyte/mixed conductor interface.

Another observation of i-V characteristics of the sensors is the observation of a peak at the beginning of the limiting-current plateau. This peak is observed only at the current plateaus for low oxygen concentrations. This may be caused by a change in the stoichiometry of the metal oxide before reaching the limiting-current plateau.

Figure 4:
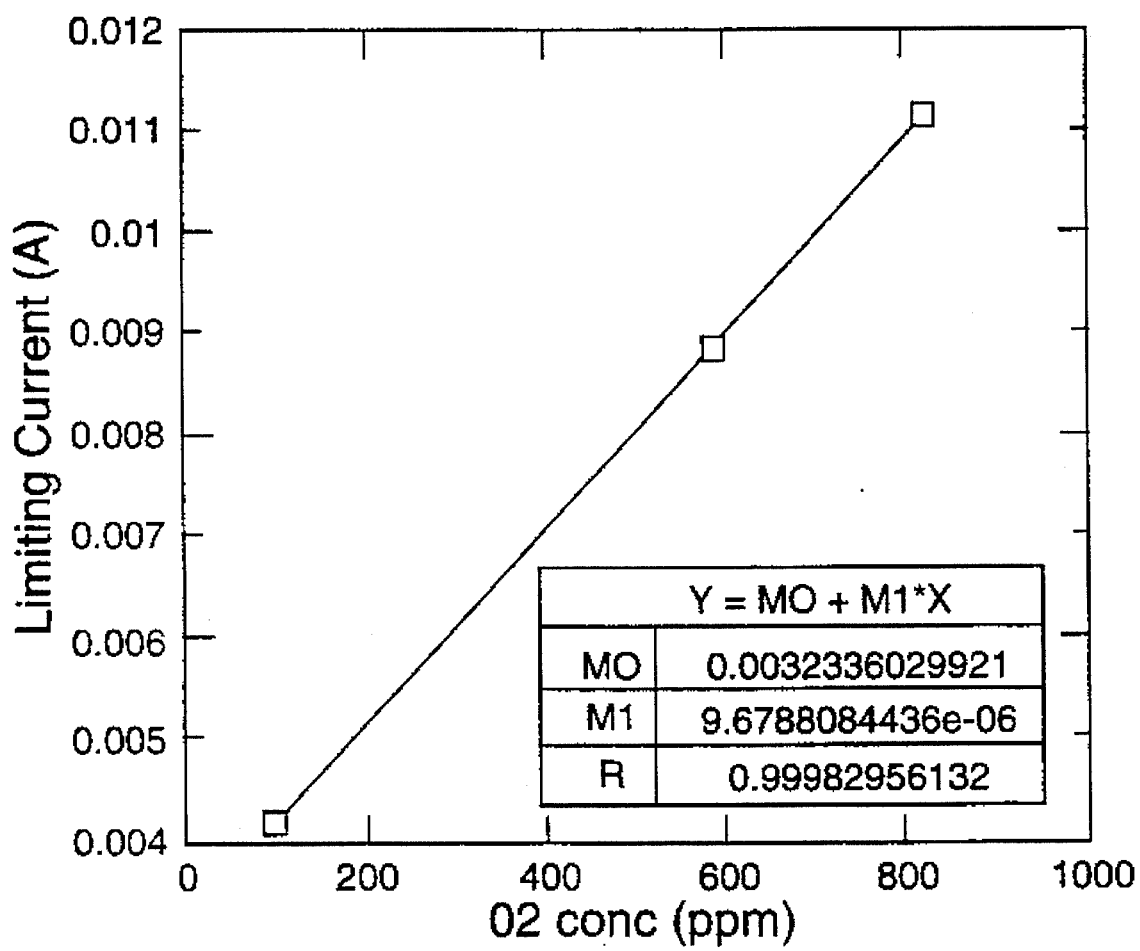
FIG. 4 graphically depicts the linear response of a sensor having the i-V characteristics shown in FIG. 3.

The fourth regime is the i-V characteristic beyond the limiting current plateau. This region is caused by the electrochemical decomposition of the electrolyte and is most dramatic at the highest operating temperatures. FIG. 4 demonstrates the linear response of the sensor having the i-V characteristic curves depicted. The best fit curve is given by Y=M0+M1* X, where Y is the limiting current value in amperes, X is the oxygen concentration in ppm, M0 is the Y intercept and M1 is the slope. A steep slope is needed for very sensitive instruments, where a shallower slope is desired for instruments that cover a wider range of oxygen concentration. A measure of the linearity of the data is the correlation factor R that correlates the data to the linear relationship. A perfect fit would be R+1. A suitable linear relationship for an oxygen sensor is given by R> about 0.9.

Tables A–G below present exemplary results showing the linear relationship between plateau currents and oxygen concentration using perovskite mixed conductors of LSMO and LSCO; solid electrolytes of yttria-doped zirconia; thin films of mixed conductors and electrolyte on an alumina substrate; and a mixed conductor on an alternate, yttria-doped zirconia electrolyte (CeraFlex). The linear relationships were explored at various temperatures (600° C., 700° C., and 800° C.) and film thicknesses as noted.

TABLE A

| | LSMO on Yttria-doped Zirconia | | |
|---|---|---|---|
| T °C. | t (μm) | 1 | 1.6 |
| 600 | M0 | 0.00323 | 0.002198 |
| | M1 | 0.96788e-05 | 0.79805e-05 |
| | R | 0.99983 | 0.99979 |
| 700 | M0 | 0.00611 | |
| | M1 | 1.22234e-05 | |
| | R | 0.99976 | |
| 800 | M0 | 0.01026 | |
| | M1 | 1.25656e-05 | |
| | R | 0.99974 | |

TABLE B

LSMO on Yttria-doped Zirconia

| T °C. | t (μm) | .49 | .6705 | .921 |
|---|---|---|---|---|
| 600 | M0 | 0.00324 | 0.00382 | 0.00396 |
|  | M1 | .7938e-05 | 1.0126e-05 | 1.1115e-05 |
|  | R | 0.99663 | 0.9867 | 0.9989 |
| 700 | M0 | 0.00273 |  | 0.00942 |
|  | M1 | 1.3752e-05 |  | 1.3689e-05 |
|  | R | 0.9938 |  | 0.99994 |
| 800 | M0 | 0.00213 |  | 0.01479 |
|  | M1 | 1.4497e-05 |  | 2.2192e-05 |
|  | R | 0.99216 |  | 0.9985 |

TABLE C

LSCO on Yttria-doped Zirconia

| T °C. | t (μm) | <.20 |
|---|---|---|
| 650 | M0 | 0.0002 |
|  | M1 | .7163e-05 |
|  | R | 0.9994 |
| 750 | M0 | 0.00015 |
|  | M1 | .8446e-05 |
|  | R | 0.9964 |

TABLE D

LSCO on Yttria-doped Zirconia

| T °C. | t (μm) | .695 |
|---|---|---|
| 600 | M0 | 0.00525 |
|  | M1 | 1.0807E-05 |
|  | R | 0.9999 |
| 700 | M0 | 0.00776 |
|  | M1 | 1.2148E-05 |
|  | R | 0.9996 |

TABLE E

LSCO on Yttria-doped Zirconia

| T °C. | t (μm) | 1.7 |
|---|---|---|
| 600 | M0 | 0.00102 |
|  | M1 | .3388e-05 |
|  | R | 0.966 |
| 700 | M0 | 0.00055 |
|  | M1 | .7042e-05 |
|  | R | 0.995 |

TABLE F

LSMO on CeraFlex

| T °C. | t (μm) | 1 |
|---|---|---|
| 600 | M0 | 3.7187 |
|  | M1 | 0.00768 |
|  | R | 0.9998 |

TABLE G

Thin Film Yttria-doped Zirconia on LSMO - $Al_2O_3$ Support

| T °C. | t (μm) | 6.7 ($t_{LSMO}$)/ 10 ($t_{YSZ}$) | 6.7 ($t_{LSMO}$)/10 ($t_{YSZ}$) Inverted |
|---|---|---|---|
| 600 | M0 | 0.00455 | 0.00407 |
|  | M1 | .2891e-05 | .2663e-05 |
|  | R | 0.9948 | 0.9899 |

In addition to lanthanum-containing perovskite mixed conductors, linear oxygen sensing has also been obtained from a zirconia-containing fluorite mixed conductor, $Zr_{0.62}Tb_{0.30}Y_{0.08}O_{3-y}$(Tb-YSZ), as shown in Table H.

TABLE H

Tb-YSZ Diffusion Barrier on Yttria-doped Zirconia

| T °C. | t (μm) | 100 |
|---|---|---|
| 740 | M0 | 0.0000443 |
|  | M1 | .05964e-05 |
|  | R | 0.9978 |

The dynamic range for these limiting current solid state oxygen sensors is determined by a number of device parameters. The range of oxygen concentration detected is larger with higher temperatures because of higher conductivity of the solid electrolyte with increasing temperature. The range can be increased significantly by using thin-film technology to form a multilayer thin-film sensor on a porous substrate (FIG. 2 and Table G) so that oxygen is pumped through the device and passed through to the ambient gas environment.

The oxygen sensor response can be further optimized by tailoring the thickness of the barrier layer for the oxygen concentration range that is desired. The mixed conductors used as diffusion barriers for our exemplary oxygen sensors had a relatively high oxygen diffusion coefficient. The high mobility of oxygen through the mixed conductor diffusion barrier limits the sensor's detection range at the currently used thicknesses.

To increase the range of the detection range, the thickness of the diffusion barrier layer can also be increased with currently available thick film technology such as screen printing. A LSMO mixed conductor was mixed with glycerin to form an ink that was screen printed on a substrate. The performance of the sensor is shown in Table I. Table I is not directly comparable to the other Tables since oxygen concentration is determined in % partial pressure rather than in parts-per-million (PPM). However, the sensitivity of the device, as measured by the slope, M1, is quite high compared to thinner film devices.

TABLE I

Glycerin-deposited LSMO on Yttria-doped Zirconia

| T °C. | t (μm) | 100 |
|---|---|---|
| 700 | M0 | 0.00011459 |
|  | M1 | 34.701e-05 |
|  | R | 0.99996 |

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A solid-state sensor for determining the concentration of oxygen in a gas, said sensor comprising:

a solid oxide electrolyte substrate defining at least one surface;

a mixed conductor film selected from the group consisting of lanthanum-containing perovskite and zirconia-containing fluorite disposed on said surface of said substrate for limiting the rate of oxygen diffusion to said solid oxide electrolyte substrate and contacting said solid oxide electrolyte substrate to form a dense diffusion barrier; and electrodes contacting said solid oxide electrolyte substrate and said mixed conductor film for applying a voltage and transporting a current therebetween.

2. A sensor according to claim 1, wherein said lanthanum-containing perovskite mixed conductor is selected from the group consisting of lanthanum strontium manganese oxide and lanthanum strontium cobalt oxide.

3. A sensor according to claim 2, wherein said electrolyte is a yttria-doped zirconia.

4. A sensor according to claim 1, wherein said electrolyte is a yttria-doped zirconia.

5. A sensor according to claim 1, wherein said electrolyte is comprised of a thin film of solid oxide electrolyte formed on a porous substrate.

6. A sensor according to claim 5, wherein said lanthanum-containing perovskite mixed conductor is selected from the group consisting of lanthanum strontium manganese oxide and lanthanum strontium cobalt oxide.

7. A sensor according to claim 5, wherein said electrolyte is a yttria-doped zirconia.

8. A sensor according to claim 7, wherein said lanthanum-containing perovskite mixed conductor is selected from the group consisting of lanthanum strontium manganese oxide and lanthanum strontium cobalt oxide.

9. A sensor according to claim 1, wherein said mixed conductor is deposited on a porous support and said electrolyte is deposited on said mixed conductor.

10. A sensor according to claim 9, wherein said lanthanum-containing perovskite mixed conductor is selected from the group consisting of lanthanum strontium manganese oxide and lanthanum strontium cobalt oxide.

11. A sensor according to claim 9, wherein said electrolyte is a yttria-doped zirconia.

12. A sensor according to claim 11, wherein said lanthanum-containing perovskite mixed conductor is selected from the group consisting of lanthanum strontium manganese oxide and lanthanum strontium cobalt oxide.

13. A sensor according to claim 1, wherein said zirconia-containing fluorite mixed conductor is terbia-yttria stabilized zirconia.

14. A sensor according to any one of claims 1–13, further including a heater to maintain said mixed conductor of said sensor at a temperature of at least 600°0 C.

* * * * *